(12) United States Patent
Esterberg et al.

(10) Patent No.: US 11,133,104 B2
(45) Date of Patent: Sep. 28, 2021

(54) DISPLAYING RELEVANT DATA TO A USER DURING A SURGICAL PROCEDURE

(71) Applicant: NAVLAB HOLDINGS II, LLC, Seattle, WA (US)

(72) Inventors: Justin Esterberg, Mercer Island, WA (US); Jeffrey Roh, Seattle, WA (US)

(73) Assignee: NAVLAB HOLDINGS II, LLC, Seattle, WA (US)

( * ) Notice: Subject to any disclaimer, the term of this patent is extended or adjusted under 35 U.S.C. 154(b) by 236 days.

(21) Appl. No.: 16/028,618

(22) Filed: Jul. 6, 2018

(65) Prior Publication Data
US 2019/0013099 A1 Jan. 10, 2019

Related U.S. Application Data

(60) Provisional application No. 62/530,128, filed on Jul. 8, 2017.

(51) Int. Cl.
| | |
|---|---|
| *G16H 40/63* | (2018.01) |
| *G16H 20/40* | (2018.01) |
| *G06F 3/01* | (2006.01) |
| *G16H 40/20* | (2018.01) |
| *G16H 10/60* | (2018.01) |

(52) U.S. Cl.
CPC ............ *G16H 40/63* (2018.01); *G16H 10/60* (2018.01); *G16H 20/40* (2018.01); *G16H 40/20* (2018.01)

(58) Field of Classification Search
CPC ........ G16H 80/00; G16H 10/60; G16H 70/20; G16H 40/63; G06N 20/00; G06N 55/022; G06F 40/30; G06F 3/017; G06F 16/23; G06F 3/011; G06F 3/0304; G06F 3/0482; G06F 3/04842; G06F 21/32; G06F 3/0488; G06F 21/31; G06F 16/183; G06K 9/00355; G06K 9/00335; G06K 9/00268; G06K 9/00288; G06K 2009/00939
See application file for complete search history.

(56) References Cited

U.S. PATENT DOCUMENTS

| | | | | |
|---|---|---|---|---|
| 8,217,759 | B2* | 7/2012 | Tessier | ...................... G01S 5/02 |
| | | | | 340/10.1 |
| 2013/0159939 | A1* | 6/2013 | Krishnamurthi | ........ G06F 3/011 |
| | | | | 715/863 |
| 2015/0332196 | A1* | 11/2015 | Stiller | .............. G06Q 10/06316 |
| | | | | 705/2 |

(Continued)

*Primary Examiner* — Maroun P Kanaan
(74) *Attorney, Agent, or Firm* — Hamre, Schumann, Mueller & Larson, P.C.

(57) ABSTRACT

The presentation of relevant data to users during a surgical procedure is disclosed. A system may include a plurality of displays present in an operating room. A medical personnel database may store data related to roles of users. A role gesture database may store gestures that may be made to store and retrieve data during the surgical procedure, based on respective roles of the users. A display tracking module may identify locations of the plurality of displays present in the operating room. A user tracking module may identify locations of the users and the occurrence of corresponding gestures of the users present in the operating room, to determine an identity of the user present in proximity to a display of the plurality of displays, and to display data related to the identity of the user based on a gesture during the surgical procedure.

16 Claims, 3 Drawing Sheets

(56) References Cited

U.S. PATENT DOCUMENTS

2016/0071341 A1* 3/2016 Menzel .................. A61B 5/00
    340/5.61
2016/0378939 A1* 12/2016 Baumberger .. G06Q 10/063114
    705/2

* cited by examiner

DISPLAYING RELEVANT DATA TO A USER DURING A SURGICAL PROCEDURE

CROSS-REFERENCE TO RELATED APPLICATION

This Application claims benefit of provisional Application Ser. No. 62/530,128 filed on Jul. 8, 2017. The disclosure of which is hereby incorporated herein by reference in its entirety.

FIELD OF THE DISCLOSURE

The present disclosure is generally related to providing surgical assistance by displaying relevant data to a user during the procedure.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Medical care centers use medical information, e.g., medical records of the patients, and medical images during treatment of the patients. The medical information may be shared between users, e.g., doctor, nurse, or anaesthesiologist, during the treatment of the patients, and the medical information may be provided to the respective users during treatment, which may include a surgical procedure. However, the medical information provided to the respective users does not take into consideration the respective roles of the users, and thus may lead to a cumbersome task for the respective users to filter through the medical information, per their respective roles.

Further, the respective users may choose to store the medical information in various forms such as physical files, written displays, common boards, and electronic systems; and may maintain a record by inputting the medical information into various forms. For example, anesthesiologists may use a white board to track patients being treated, but such type of records may be difficult to access or maintain during a surgical procedure. As another example, during a surgical procedure, surgeons may use an input apparatus such as keyboard, mouse, etc., by stepping away from an operating table to input and/or access the medical information. Such activities may delay the surgical procedure and may increase risks of adverse effects, e.g., spreading infection-causing bacteria.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
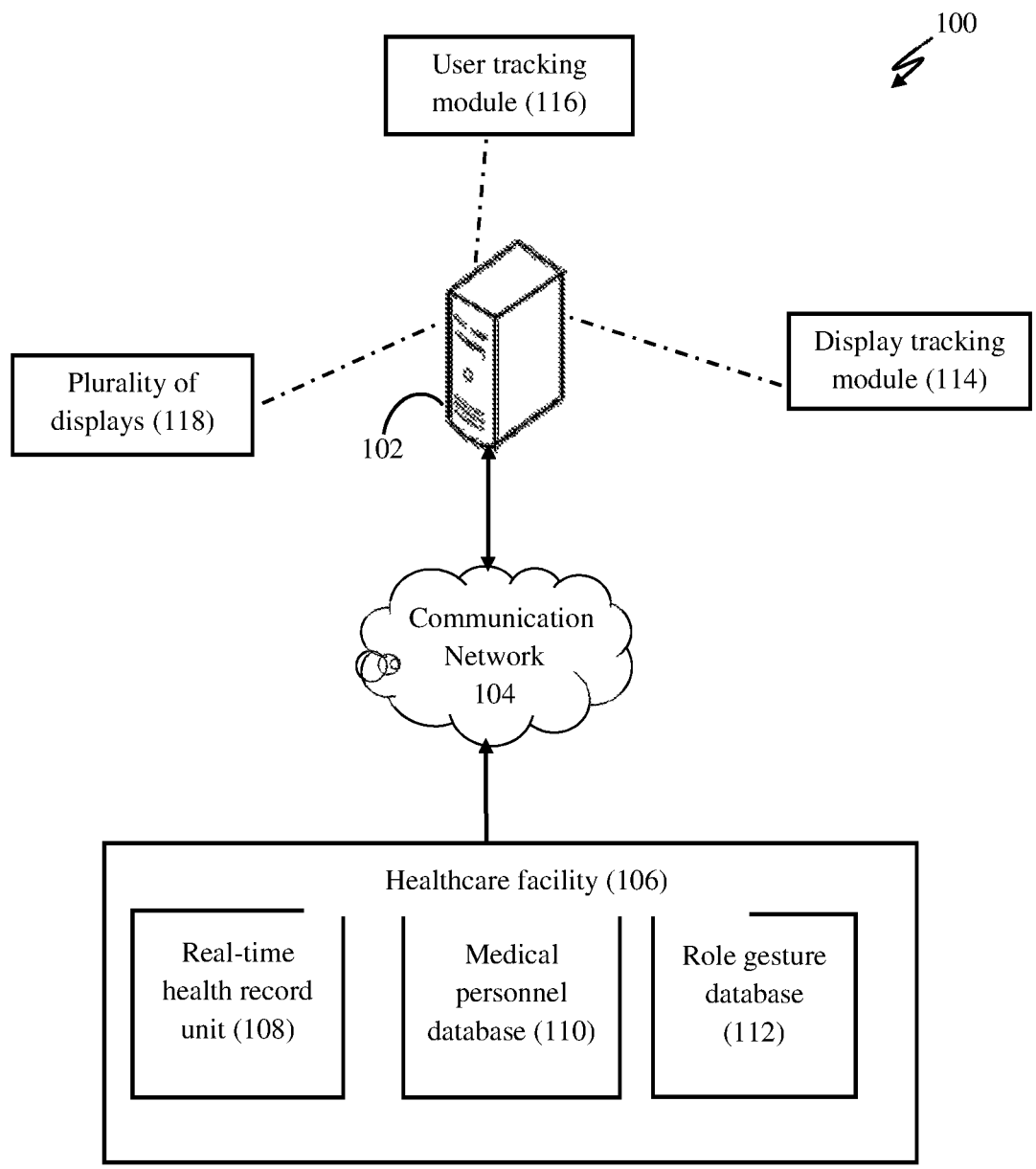
FIG. 1 shows a network connection diagram 100 of a system 102 to display relevant data to a user during a surgical procedure, according to an embodiment.

FIG. 1 shows a network connection diagram 100 of a system 102 to display relevant data to a user, during a surgical procedure, according to an embodiment. The system 102 may be connected to a communication network 104. The communication network 104 may further be connected with a healthcare facility 106 to facilitate data transfer therebetween.

The communication network 104 may be a wired and/or a wireless network. The communication network 104, if wireless, may be implemented using communication techniques such as Visible Light Communication (VLC), Worldwide Interoperability for Microwave Access (WiMAX), Long Term Evolution (LTE™), Wireless Local Area Network (WLAN), Infrared (IR) communication, Public Switched Telephone Network (PSTN), Radio waves, and other communication techniques known in the art.

The healthcare facility 106 may include a real-time health record unit 108 and a group of databases for storing different information that may be required during the surgical procedure. The group of databases may include a medical personnel database 110 and a role gesture database 112, which are illustrated as being separate databases but could be integrated in a single database in alternative embodiments.

However, usage of the different databases may facilitate segregated storage of different data, thus reducing access time.

The real-time health record unit 108 may be configured to store data of patients in real-time, in accordance with a surgical procedure. The data may correspond to medical imaging data, and/or diagnostic data, e.g., medical records of respective patients, including but not limited to medical charts, test results, and notes of surgeons/doctors or other medical providers with whom a respective patient has consulted.

In at least one embodiment, the medical personnel database 110 may be configured to store data related to respective users of healthcare facility 106 including, but not limited to, doctors of various specialties, e.g., anaesthesiologists, and other surgery participants, etc. The data may specify one or more roles of the respective users during particular surgical procedures, responsibilities of the respective users during particular surgical procedures, and information (stored in Electronic Health Record (EHR)) relevant for the respective users in accordance with an assigned role in any surgical procedure. For example, if a user is an anaesthesiologist, then information may be related to pulse oxygen levels that may be relevant for the anaesthesiologist during a specified type of surgical procedure.

In an embodiment, the role gesture database 112 may be configured to store a library of gesture commands corresponding to the respective users, for a gesture interface, as they participate in a surgical procedure. That is, the gesture interface may include one or more gestures that correspond to different roles of surgery participants and/or attendees. For example, a surgeon may utilize a different of gestures while using a particular surgical tool, while an anaesthesiologist may utilize a different gestures during the same surgical procedure due to the different roles and, therefore, different tools. Further, the role gesture database 112 may include multiple images that may be classified by a respective user, based on a gesture of the respective user. For example, a surgeon may use a head node to select a stored image during a surgical procedure.

In one embodiment, the role gesture database 112 may be configured to store situational rules for respective users participating in or attending a surgical procedure. The situation rules may be provided to a relevant user on one or more of a plurality of displays 118. Examples of the situational rules may include a nurse having a top-priority to clean up instruments at an end of the surgical procedure; the surgeon may have a top-priority function at the occurrence of an adverse event during the surgical procedure; etc.

Figure 2:
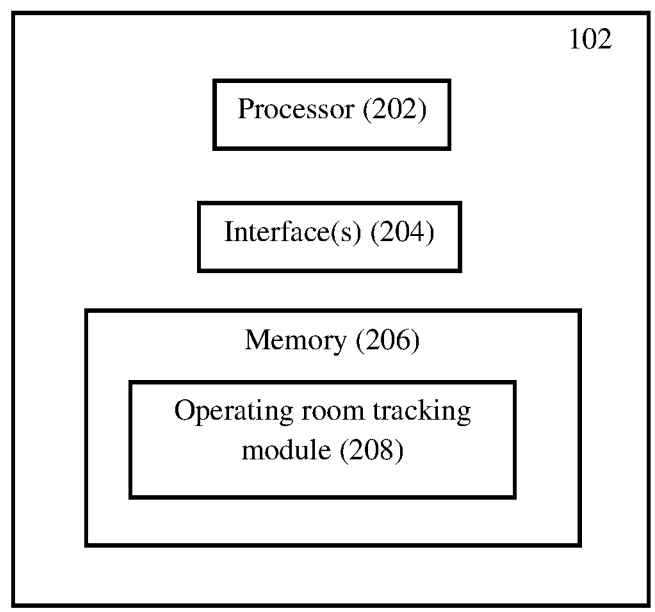
FIG. 2 shows a block diagram of components of the system 102, according to an embodiment.

FIG. 2 shows a block diagram of different components of the system 102, according to at least one embodiment. The system 102 includes a processor 202, interface(s) 204, and a memory 206. The processor 202 may be configured to execute an algorithm stored in the memory 206 to relevant data to respective users during a surgical procedure. The processor 202 may also be configured to decode and execute any instructions received from one or more other electronic devices or server(s). The processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be further configured to execute one or more computer-readable program instructions, such as program instructions to carry out any of the functions described in this description.

The interface(s) 204 may be configured to facilitate interaction between the respective users participating in or attending a surgical procedure and the system 102. The interface(s) 204 of the system 102 may accept input from the user and/or provide an output to the user. The interface(s) 204 may either be a Command Line Interface (CLI), Graphical User Interface (GUI), or a voice interface.

The memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions. In at least one embodiment, the memory 206 may include an operating room tracking module 208.

Figure 3:
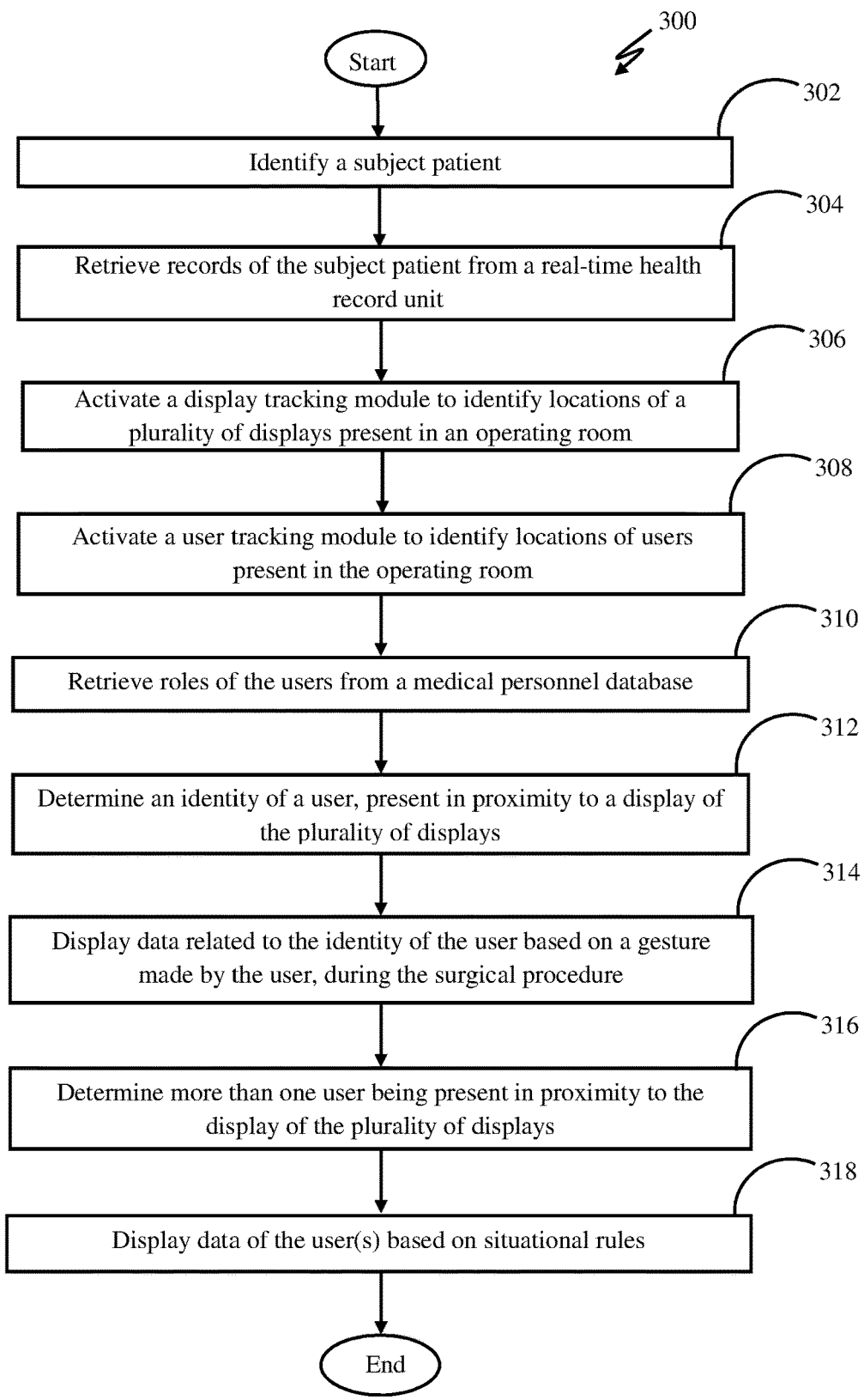
FIG. 3 shows a flowchart 300 showing a method to provide relevant data to respective users during a surgical procedure, according to an embodiment.

FIG. 3 shows a flowchart 300 for a method to provide relevant data to respective users during a surgical procedure, as executed by operating room tracking module 208, in accordance with at least one embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

At first, a user may log-in to the system 102 using one or more personal credentials, e.g., a user name, a password, biometric credentials, etc. At step 302, the user may verify the identify the subject patient using the operating room tracking module 208. The subject patient may refer to a patient that needs to be operated on.

At step 304, records of the subject patient may be retrieved from the real-time health record unit 108. The records may include medical data related to a medical condition of the subject patient, including, e.g., one or more medical images of an affected body part of the subject patient.

At step 306, a display tracking module 114 may be activated. The display tracking module 114 may be configured to identify locations of a plurality of displays 118 present in an operating room e.g., the display tracking module 114 may be mounted in a ceiling of the operating room.

At step 308, the operating room tracking module 208 may activate a user tracking module 116, which may be configured to identify locations of the respective users present in the operating room. In at least one example, the user tracking module 116 may also be mounted in the ceiling of the operating room.

At step 310, information regarding one or more roles of the respective users from the medical personnel database 110. For example, for an anaesthesiologist participating in a particular surgical procedure, information regarding the pulse oxygen levels to be administered to the subject patient may be retrieved.

At step 312, an identity of the respective users from among the one or more users may be determined. The identity of a particular user may be determined based on a presence of a respective user in proximity to a particular one of the plurality of displays 118.

At step 314, relevant data related to the identity of a respective user may be displayed. The displayed relevant data related to the identity of the user may be displayed in response to a gesture made by the user, e.g., hand-wave, head nod, during the surgical procedure. Further, the relevant data may be displayed on at least one of the plurality of displays 118, and the gesture may correspond to a role of the user. For example, if a particular user is an anaesthesiologist, then data such as pulse oxygen levels may be displayed on a display proximate to the head of the subject patient. If a user is a nurse, then, for example, the patient's vital statistics along with surgical tools may be displayed on a display proximate to the nurse. In response, the nurse may prepare and position the surgical tools properly for a surgeon to perform next steps in a surgical procedure.

At step 316, the operating room tracking module 208 may repeatedly check to determine whether more than one user is in close proximity to a particular one of the plurality of displays 118.

At step 318, upon a positive determination at step 316, the operating room tracking module 208 may display data of the user(s) based on one or more situational rules. For example, if both the surgeon and the nurse are present in substantially equal proximity to a particular display, then the display may provide the data specific to situational rules of both users, e.g., the displayed data may show that the nurse has a top-priority responsibility to clean-up at an end of the surgical procedure, and may further show that the surgeon has certain top-priority responsibilities upon occurrence of an adverse event in the surgical procedure. The displayed data may also make reference to the users present in proximity to the particular display, an amount of time spent by each user in front of the particular display, and one or more gestures of the users having a lower permission level.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A system for displaying customized data to respective personnel during a team operation in an operating room, the system comprising:
    a personnel database configured to store data corresponding to the respective personnel;
    a gesture database configured to store gesture commands for an interface that corresponds the gesture commands to the roles of the respective personnel simultaneously in the operating room;
    a display tracking device, mounted within the operating room, configured to track locations of plural displays; and
    a user tracking device, mounted within the operating room, configured to:
        identify locations of the respective personnel within the operating room,
        determine a presence of one or more of the respective personnel in proximity to respective ones of the plural displays,
        retrieve data regarding one or more roles of the respective personnel from the personnel database,
        identify the respective ones of the personnel based on the determined presence in proximity to respective ones of the plural displays,
        identify the one or more gestures made by respective ones of the personnel, and
        display the retrieved data for the identified personnel, on a respective one of the displays proximate to the identified personnel and corresponding to the role of the identified personnel, based on the identified gestures corresponding to the role of the identified personnel.

2. The system of claim 1, wherein the stored data corresponding to one or more gestures corresponding to the respective personnel associates data to be displayed for each of the respective personnel upon detection of respective ones of the gestures.

3. The system of claim 1, wherein the user tracking device is configured to display the data corresponding to respective ones of the personnel upon detection of respective ones of the gestures.

4. The system of claim 1, wherein the user tracking device is configured to display the data corresponding to respective ones of the personnel upon occurrence of previously annotated events during a surgical procedure.

5. The system of claim 1, wherein the user tracking device is configured to identify the locations of the respective personnel by detecting unique radio frequency (RF) signals emanating from sensors worn by each of the respective personnel.

6. The system of claim 1, wherein the user tracking device is configured to identify the gestures made by respective ones of the personnel by sensors attached to respective ones of the plurality of displays determined to be in proximity to the respective personnel.

7. The system of claim 6, wherein the sensors are video cameras or motion detectors.

8. A non-transitory computer-readable storage medium having executable components stored thereon, the components comprising:
    a display tracking module configured to track locations of plural displays within a room; and
    a user tracking module configured to:
        identify locations of respective ones of multiple personnel within the room,
        detect a presence of one or more of the respective personnel in proximity to respective ones of the plural displays;
        retrieve data regarding one or more roles of the respective personnel from a personnel database,
        identify respective ones of the detected personnel,
        identify one or more gestures made by the respective ones of the personnel, and
        display the retrieved data for the identified personnel, on a respective one of the displays proximate to the identified personnel and corresponding to the role of the identified personnel, based on the identified gestures by matching identified gestures to roles of the identified personnel.

9. The computer-readable medium according to claim 8, wherein the user tracking module is configured to retrieve data corresponding to the one or more gestures from a local memory.

10. The computer-readable medium according to claim 8, wherein the data corresponding to the one or more gestures associates specific ones of the gestures to respective ones of the personnel.

11. The computer-readable medium of claim 8, wherein the user tracking module is configured to display the data corresponding to respective ones of the personnel upon detection of respective ones of the gestures.

12. The computer-readable medium of claim 8, wherein the user tracking module is configured to display the data corresponding to respective ones of the personnel upon occurrence of previously annotated events during a surgical procedure.

13. The computer-readable medium of claim 8, wherein the user tracking module is configured to identify the locations of the respective personnel by detecting unique radio frequency (RF) signals emanating from sensors worn by each of the respective personnel.

14. The computer-readable medium of claim 8, wherein the user tracking module is configured to identify the gestures made by respective ones of the personnel by sensors attached to respective ones of the plurality of displays determined to be in proximity to the respective personnel.

15. The computer-readable medium of claim 14, wherein the sensors comprise video cameras.

16. The computer-readable medium of claim 14, wherein the sensors comprise motion detectors.

* * * * *